United States Patent
Radmacher et al.

(10) Patent No.: US 6,740,294 B2
(45) Date of Patent: May 25, 2004

(54) METHOD FOR THE ANALYSIS OF GASEOUS COMPONENTS AND TEST KIT, IN PARTICULAR TEST KIT FOR THE IMPLEMENTATION OF THIS METHOD

(75) Inventors: Edmund Radmacher, Duren (DE); Klaus Moller, Eschweiler (DE); Fritz Niendieck, Aachen (DE)

(73) Assignee: Macherey, Nagel GmbH & Co., Duren (DE)

( * ) Notice: Subject to any disclaimer, the term of this patent is extended or adjusted under 35 U.S.C. 154(b) by 386 days.

(21) Appl. No.: 09/835,117

(22) Filed: Apr. 16, 2001

(65) Prior Publication Data
US 2001/0051378 A1 Dec. 13, 2001

(51) Int. Cl.[7] .......................... G01N 7/00; G01N 21/00; G01N 27/00; G01N 31/00; G01N 33/00
(52) U.S. Cl. .............. 422/83; 422/50; 422/52; 422/55; 422/58; 422/61; 422/68.1; 422/80; 422/83; 73/1.01; 73/1.02; 73/19.01; 73/23.2; 73/23.35; 436/2; 436/8; 436/43; 436/56; 436/164; 436/174
(58) Field of Search ................... 422/83, 50, 52, 422/55, 58, 61, 68.1, 80; 73/1.01, 1.02, 19.01, 23.2, 23.35; 436/2, 8, 43, 56, 164, 174

(56) References Cited

U.S. PATENT DOCUMENTS

| | | | | |
|---|---|---|---|---|
| 2,768,879 A | * | 10/1956 | Hewson | 422/64 |
| 3,713,779 A | * | 1/1973 | Sirago et al. | 422/61 |
| 3,715,189 A | * | 2/1973 | Nighohossian et al. | 422/61 |
| 4,315,890 A | | 2/1982 | Tamers | 422/61 |
| 4,324,758 A | * | 4/1982 | Eisentraut et al. | 422/61 |
| 5,320,807 A | | 6/1994 | Brinton | 422/61 |
| 5,413,763 A | * | 5/1995 | Jeffers | 422/80 |
| 5,979,219 A | | 11/1999 | Sellmer-Wilsberg et al. | 73/19.12 |

FOREIGN PATENT DOCUMENTS

| | | |
|---|---|---|
| DE | 2712158 | 9/1978 |
| DE | 19616760 | 11/1997 |
| EP | 0663239 | 7/1995 |
| WO | 9942824 | 8/1999 |

OTHER PUBLICATIONS

Gerhart Jander and Ewald Blasius, "Lehrbuch der analystischen und praparativen anorganischen Chemie", S. Hirzel Verlag Stuttgart, 1989, pp. 135–137, Germany.

* cited by examiner

Primary Examiner—Jill Warden
Assistant Examiner—Brian Sines
(74) Attorney, Agent, or Firm—Liniak, Berenato & White, LLC

(57) ABSTRACT

The present invention relates to a method for the analysis of a gaseous component or of a component that can be transformed into gaseous form (23) of a sample (5) which provides that the sample (5) is filled into a sample receptacle (2) through a receptacle opening (4), and an analysis receptacle (7), which was previously supplied with a tracer reagent, is then by way of its receptacle opening (4) connected with the receptacle opening (4) of sample receptacle (2) via an adapter (10), after which step the component (23) is expelled from the sample receptacle (2) and into the analysis receptacle (7) wherein the analysis receptacle (7) is connected with the outside atmosphere in such a manner that a pressure compensation can take place.

The invention further relates to a test kit, in particular, a test kit for implementing the method.

24 Claims, 2 Drawing Sheets

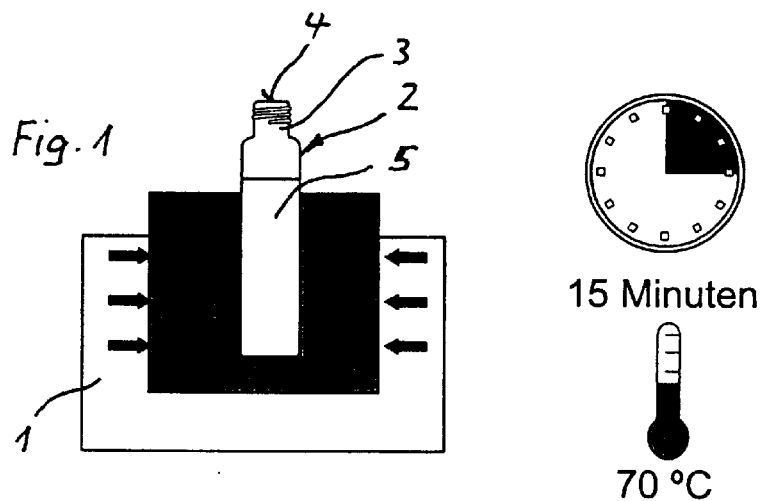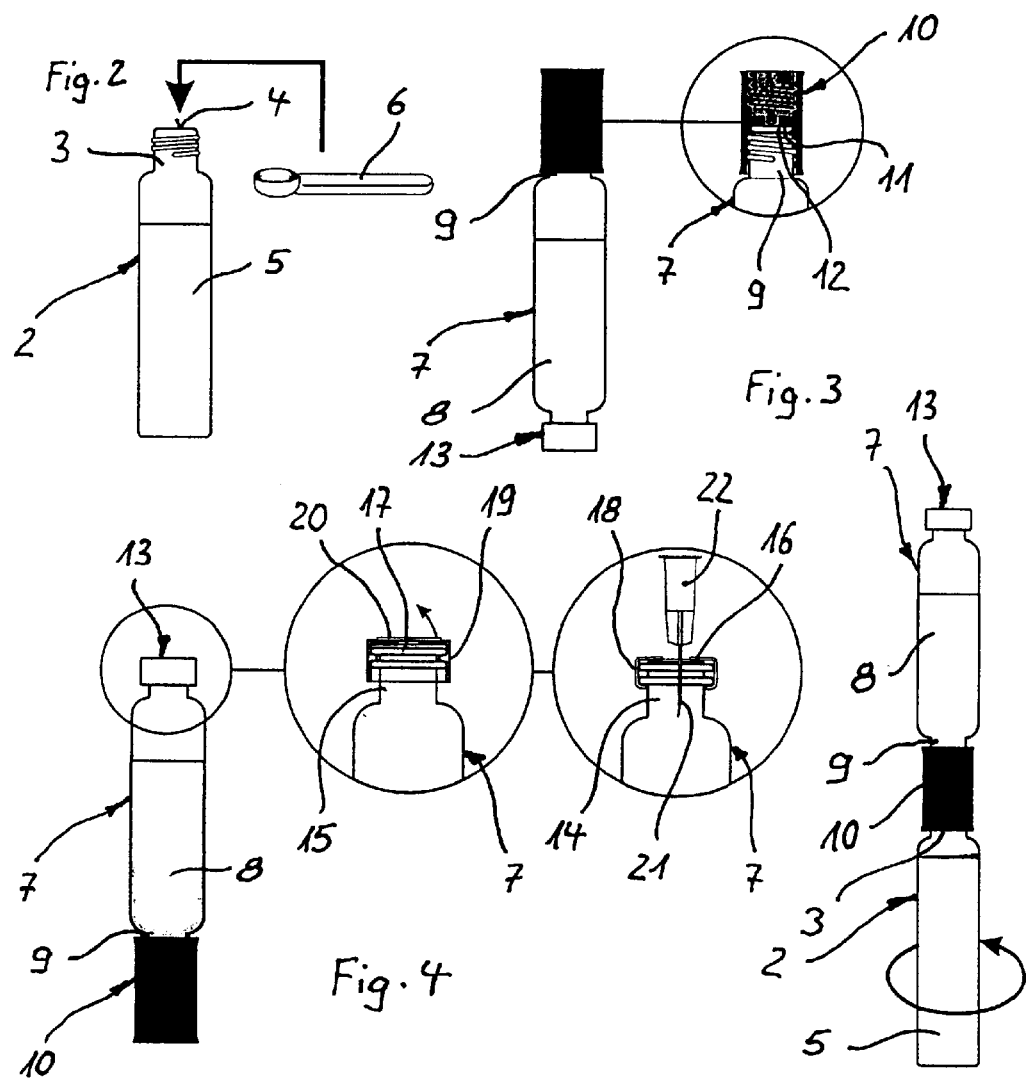

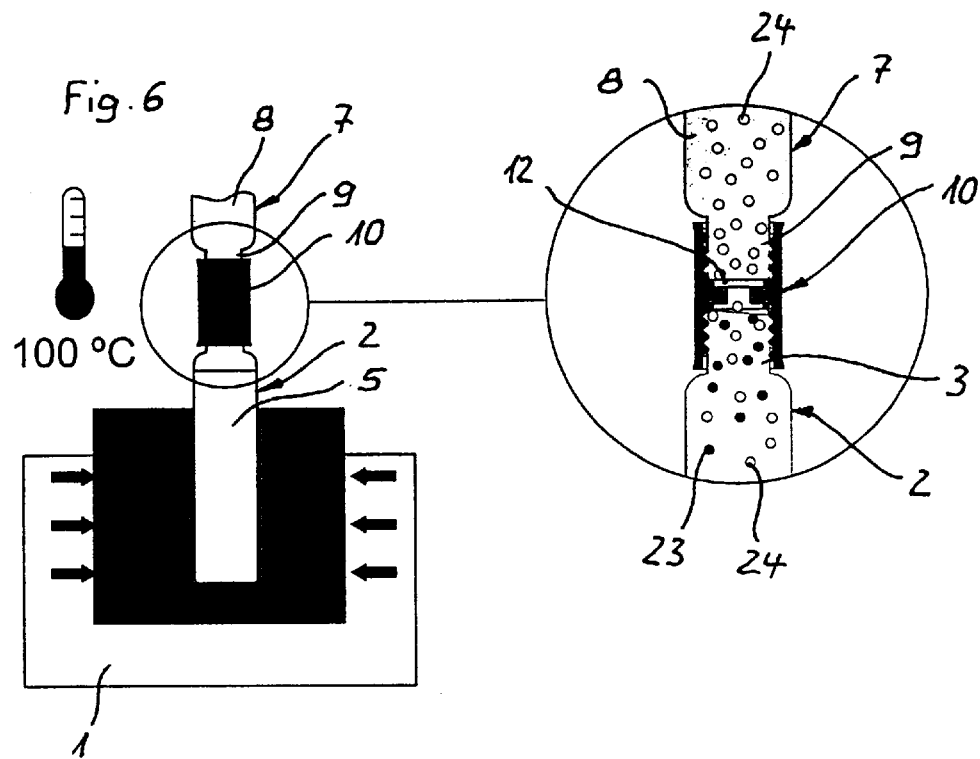
Fig. 6
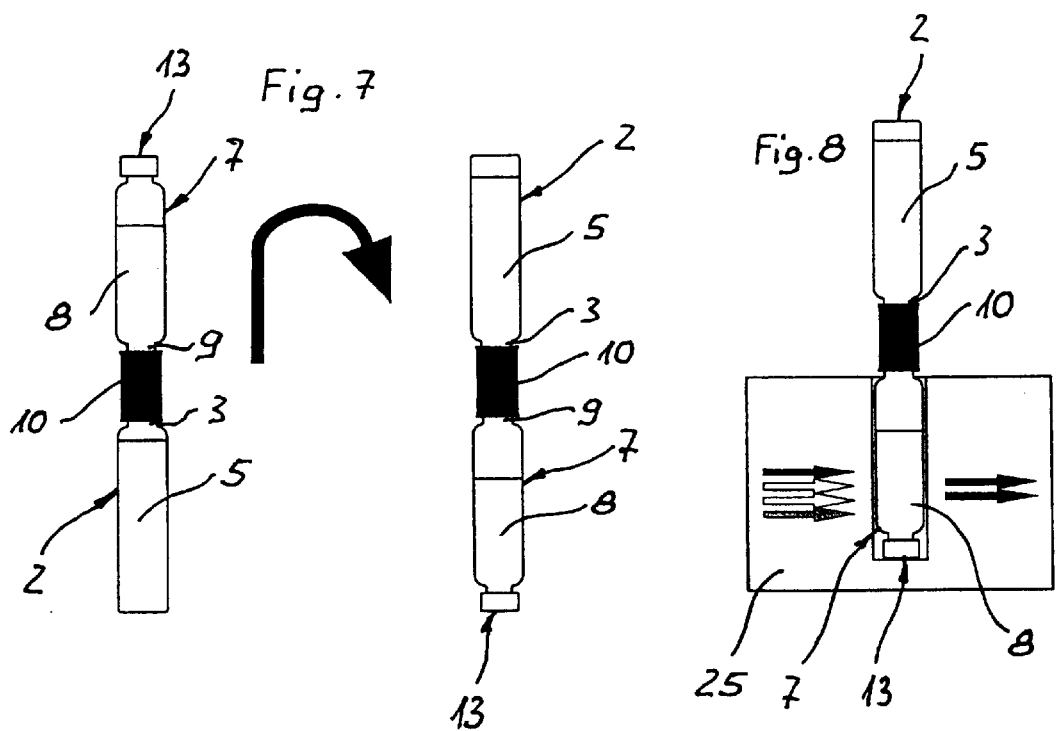
Fig. 7
Fig. 8

METHOD FOR THE ANALYSIS OF GASEOUS COMPONENTS AND TEST KIT, IN PARTICULAR TEST KIT FOR THE IMPLEMENTATION OF THIS METHOD

The invention relates to a method for the analysis of a gaseous component or of a component that can be transformed to gaseous form of a sample. The method provides that the sample is filled into the sample receptacle through the receptacle opening and that an analysis receptacle, which was previously supplied with a tracer reagent, is connected by its receptacle opening via an adapter with the receptacle opening of the sample receptacle, and after which step the component from the sample is expelled into the analysis receptacle. The invention relates, furthermore, to a test kit, in particular a test kit for the implementation of the method described above consisting of the sample receptacle for receiving the sample through a receptacle opening and of an analysis receptacle for receiving the component that is to be analyzed through a receptacle opening, with the analysis receptacle containing a tracer reagent or being able to be supplied with a tracer reagent and being usable as measuring receiving flask in an optical measuring instrument, as well as of an adapter that is used to connect the openings of the receptacles with each other.

It is known in the field of water analytics that certain components in a water sample can be selectively separated from the sample by transforming the components into their gaseous form and to analyze them after this, either directly or indirectly—in the latter case with optical analysis instruments such as, for example, a photometer. This is done in particular for the determination of carbon; and in this context, the total organic carbon (TOC) is of particular interest. The TOC determination is carried out principally in accordance with DIN EN 1484.

As a rule, the component of the sample is treated in such a manner that the TOC—after prior removal of the inorganic carbon (TIC)—is transformed in the presence of an oxidant, e.g. sodium peroxodisulfate, into its gaseous form, i.e. $CO_2$, and is then expelled from the sample receptacle by way of an inert carrier gas, for example by way of steam distillation or by way of excess reaction gas, into an analysis receptacle. In the analysis receptacle the $CO_2$ is absorbed into a tracer reagent that is present in its liquid or solid form. As a result, the tracer reagent undergoes an optical change which can be analyzed using an optical analysis instrument, e.g. a photometer.

To implement this type of analytical procedure simply and quickly on location with only minimally trained personnel and inexpensive means test kits were developed, as described for example in EP 0 663 239 B1. This test kit contains two receptacles that are realized as glass cuvettes, in particular a sample receptacle and an analysis receptacle, and the receptacles have openings on their top sides respectively which can be locked with screw caps that can be screwed onto the container. The kit also includes an adapter that is to be used in order to be able to achieve a gas-proof connection of the receptacle openings with each other after the removal of the screw caps. The adapter is equipped with a semi-permeable membrane which is permeable for gases, in particular it is permeable for the component that is to be analyzed and for the carrier gas. Also, the membrane can consist e.g. of a hydrophobic material. The tracer reagent can be contained in the analysis receptacle in a previously ready-made and storable form. The sample receptacle can also be supplied with a previously ready-made decomposition reagent that will effect the transformation of the component to be analyzed into its gaseous form.

With the test kit known in the art the absorption of the component that is expelled from the sample occurs inside a closed system, consisting of the two glass cuvettes and of the adapter, which provides a gas-proof connection between the two receptacle openings. Any falsification due to penetrating air from the outside is thereby prevented, which would, due to the $CO_2$ content in the air, lead to incorrect results, in particular with regard to the TOC determination. However, it is disadvantageous that a counter-pressure develops inside the analysis receptacle that counteracts the gas exchange from the sample receptacle to the analysis receptacle and also inhibits the color change on the tracer reagent.

Therefore, it is the subject matter of the present invention to realize a method that works faster and quantitatively with more effectiveness and that results in a more intensive optical change of the tracer regent. Another subject matter of the invention is to provide a suitable test kit for implementing this method.

The first objective is achieved according to the invention in that the analysis receptacle is connected with the outside atmosphere in such a way that a pressure compensation takes place. Thus, the principal concept of the invention provides that the method is no longer—as has been known in the art—implemented inside a closed system, but that the analysis receptacle is selectively opened vis-a-vis the atmosphere while the component is being expelled and, consequently, a partial or complete pressure compensation in relation to the outside atmosphere is achieved. This accelerates the transfer of the gaseous component and of the carrier gas into the analysis receptacle and also results in better absorption of the component on the tracer reagent. In addition, this method ensures that the component reaches the analysis receptacle completely. Also, the connection with the outside atmosphere represents ultimately a kind of safety valve preventing any bursting of the container due to excess pressure.

The realization of the invention envisions that the connection with the outside atmosphere is not established until after the adapter has been attached to the analysis receptacle. This can be accomplished, for example, by removing a covering that blocks the connection.

To accomplish the pressure compensation the analysis receptacle can be perforated, for example, with a ventilation tube.

The invention further envisions that after receiving the sample the sample receptacle is heated, in particular in such a way that a component which is not to be analyzed is expelled, for example inorganic carbon. To support this process, before heating the sample receptacle should be supplied with an expulsion reagent that facilitates the expulsion. The sample receptacle can be heated in unit heaters that are known in the art.

The second part of the objective, which relates to the test kit itself, is achieved according to the invention in that the analysis receptacle is equipped with a pressure relief device, preferably arranged on the end of the analysis receptacle that is opposite to the receptacle opening. The pressure relief device should only be permeable for gases, in particular if a liquid is used as tracer reagent. Excess carrier gas escapes through the pressure relief device, thereby preventing air from entering the analysis receptacle.

The pressure relief device can be realized in a multitude of ways. A particularly simple realization envisions that it is realized as a opening in the receptacle that is closed off with a semi-permeable covering, and the covering preferably consists of a hydrophobic material. It is most useful if the covering is realized as a membrane consisting of e.g. PTFE, PVDF or FEP.

In the alternative, the pressure relief device can be realized as a closed-off opening in the receptacle equipped with a covering that can be perforated, for example in the form of a rubber membrane, in particular consisting of isobutylene-isoprene colpolymer with one-sides or two-sided PTFE or FEP coating. A ventilation tube with a very small dimensioned inside diameter that is part of the pressure relief device should be used for perforating. Since the membrane is self-closing it prevents any outflow of the tracer reagent after the ventilation tube is extracted.

In a further realization of the invention it is envisioned that the covering of the opening in the receptacle features on its outside a protective element that can be removed or pulled off, for example in the form of a paste-on protective foil. This way any gas exchange during storage and transport of the test kit is avoided.

The adapter per se is envisioned in a way that is known in the art, providing it is equipped with a separating membrane that is permeable only for gases in order to avoid any exchange of liquids between the two receptacles. The separating membrane can, for example, consist of a hydrophobic material to accomplish this.

Using the drawings, the invention is illustrated in more detail. Shown is an embodiment for the test kit as well as a representation of the way the method works. Shown are in:

FIG. 1 a sample receptacle, placed inside a unit heater;

FIG. 2 a sample receptacle while filling in the decomposition reagent;

FIG. 3 an analysis receptacle with screwed on adapter, including an enlarged sectional representation;

FIG. 4 the analysis receptacle in accordance with FIG. 3 in a position that is rotated by 180°, including two versions of pressure relief device in enlarged sectional representations;

FIG. 5 the combination of sample receptacle and analysis receptacle, connected by the adapter;

FIG. 6 the combination in accordance with FIG. 5, placed inside the unit heater, including an enlarged sectional representation of the adapter;

FIG. 7 the view of the combination seen in FIG. 5, including a representation of the same combination rotated by 180°;

FIG. 8 the combination seen in FIG. 7, placed inside a photometer.

FIG. 1 is a schematic depiction of a vertical section of a unit heater 1 of the usual build. A sample receptacle 2, realized as a round cuvette made of glass, is placed inside the unit heater 1. The sample receptacle 2 has a threaded receptacle connection piece 3 on its top side that surrounds a receptacle opening 4.

A water sample 5 mixed with an acid mixture, i.e. sodium hydrogen sulfate, is filled into the sample receptacle 2. Prior to this step the acid mixture was ready-made and contained in the sample receptacle 2. The unit heater 1 is heated to 70° C. for 15 minutes symbolized in the graphic depiction on the right—which causes inorganic carbon to be expelled.

After the inorganic carbon has been removed the sample receptacle 2 is taken out of the unit heater 1. As seen in FIG. 2, a decomposition reagent in the form of an oxidant, in the present context peroxodisulfate, is now added through the receptacle opening 4 using a measuring spoon 6.

FIG. 3 shows an analysis receptacle 7, also realized as a round cuvette made of glass, which is filled with a liquid tracer reagent 8. The analysis receptacle 7 has a receptacle connection piece 9 on its top side which surrounds a receptacle opening here as well. An adapter 10 made of plastic is screwed onto the receptacle connection piece 9.

The adapter design can be seen in the enlarged depiction of the vertical section in the right part of the figure. The adapter has the shape of a sleeve with a centrically projecting ring land 11; and internal screw threads are incorporated above and below the ring land 11. By way of the bottom internal screw thread the adapter 10 is screwed onto the receptacle connection piece 9. Clamped between the front side of the receptacle connection piece 9 and the bottom side of the ring land 11 is a hydrophobic separating membrane 12, which is permeable for gases but not for liquids and, therefore, it is not permeable for the tracer reagent 8.

A pressure relief device 13 is located on the bottom side of the analysis receptacle 7. FIG. 4 shows two possible embodied examples of this pressure relief device 13. The analysis receptacle 7 is shown there as rotated by 180°, which is why the adapter 10 is at the bottom side and the pressure relief device 13 is at the top side.

On the right side the two embodied examples of the pressure relief device 13 are framed with circles and shown as enlarged. Both pressure relief devices 13 are attached to a relief connection piece 14, 15 which forms part of the analysis receptacle 7. The relief connection pieces 14, 15 are covered on their top sides with the membranes 16, 17, that are pressed and fastened solidly, which is why they are gas-proof, to the front sides of the relief connection pieces 14, 15 with the clamping rings 18, 19. The membranes 16, 17 are impermeable for liquids making it impossible for the tracer reagent to escape even if the analysis receptacle 7 in not in the position shown in FIG. 3.

In the embodiment on the left side the membrane 17 is semi-permeable. It is permeable for the carrier gas that develops inside the sample receptacle 2 after the decomposition reagent is added (FIG. 2). The opening that is left free by the clamping ring 19 is covered on the outside with a paste-on foil 20 which protects the membrane 17 during the time before the analysis receptacle 7 is in use and forms a gas-proof barrier. Before the actual use of the analysis receptacle 7 the paste-on foil 20 is pulled off by hand, which is symbolized by the indicated arrow. The pore width of the membrane 17 is in the range of below 50 $\mu$m, preferably at 20 $\mu$m.

In the embodiment on the right side, the membrane 16 consists of rubber, which means it is liquid-proof and gas-proof. To establish a connection with the outside atmosphere the membrane 16 is perforated with a needle-shaped ventilation tube 21, whose inside diameter is 0.45 mm. The outside end of the ventilation tube 21 is located inside a handling sleeve 22.

The analysis receptacle 7 can be equipped ready-made for use inside the test kit, as shown in FIG. 3, i.e. it is already supplied with the tracer reagent 8 and the adapter 10. However, it is also possible to fill the analysis receptacle 7 with the tracer reagent 8 and screw on the adapter 10 at the time when an analysis is carried out, in particular this is done most suitably in a parallel step to filling the decomposition reagent into the sample receptacle 2.

The adapter 10 should be screwed onto the sample receptacle 2 immediately after the decomposition reagent has been added in, as depicted in FIG. 5. The analysis receptacle 7 has the position shown in FIG. 4 with the adapter 10 at the bottom, and the sample receptacle 2 is subsequently screwed into the adapter 10 from below. The adapter 10 connects the receptacle openings 4 of the sample receptacle 2 and the analysis receptacle 7 while sealing. Opening the pressure relief device 13 can take place in the sense described above either before or immediately after the sample receptacle 2 has been screwed on.

Subsequently, the unit consisting of sample receptacle 2, analysis receptacle 7 and adapter 10 is placed once again into the unit heater; however, only the sample receptacle 2 extends into the unit heater 1. This is shown in FIG. 6. Inside the unit heater 1 the water sample 5, to which was added the decomposition reagent, is heated to 100° C. The effect of the decomposition reagent and the heat is twofold. On the one hand, the remaining organic carbon is gasified and expelled from the water sample 5. On the other hand, a carrier gas 24 consisting of oxygen and steam forms which serves as a carrier for the $CO_2$ 23 and takes it, due to the resulting excess pressure, along with it upward in the direction of the analysis receptacle 7. $CO_2$ 23 and carrier gas 24 flow through the separating membrane 12 and reach the tracer reagent 8. The $CO_2$ 23 is absorbed there resulting in an optical change, for example a color change of the tracer reagent 8.

The carrier gas 24 bubbles through the tracer reagent 8, which causes it to become intermixed, and subsequently it can escape to the outside atmosphere via the pressure relief device 13. This prevents the build-up of pressure inside the analysis receptacle 7. Not only does this accelerate the gas transport into the analysis receptacle 7 but it also ensures the complete transfer of the $CO_2$ 23 to the tracer reagent 8. Moreover, the intensive bubble-through process of the carrier gas 24 increases the contact surface, thereby resulting in a more intensive color change. Finally, due to the pressure relief device 13 it is also possible to prevent the sample receptacle 2 or the analysis receptacle 7 from bursting.

After the expulsion of the $CO_2$ 23 is complete the unit consisting of sample receptacle 2 and analysis receptacle 7 is removed from the unit heater 1 and is—as shown in FIG. 7—rotated by 180° bringing the sample receptacle 2 back to the top and the analysis receptacle 7 back to the bottom. In the embodiment shown in FIG. 4, the ventilation tube 21 must be removed first, which causes the membrane 16 to close itself automatically forming a seal against any liquid. In this position the unit is placed into a photometer 25, but only the analysis receptacle 7 extends into the photometer. In this position the analysis receptacle 7 and the tracer reagent 8—symbolized by the arrows are exposed to light of a certain wavelength and the extinction that is generated by the tracer reagent 8 is recorded as a measure for the amount of the component that is absorbed by the tracer reagent, which is $CO_2$ in the present case.

What we claim is:

1. Method for the analysis of a gaseous component or of a component that can be transformed into gaseous form (23) of a sample (5) comprising filling the sample (5) into a sample receptacle (2); connecting the sample receptacle to an analysis receptacle (7) supplied with a tracer reagent, the receptacles being connected via an adapter (10); after which step, expelling the component (23) from the sample receptacle (2) and into the analysis receptacle (7); reacting the component with the tracer reagent; detecting a color change of the tracer reagent; correlating the color change with the presence of the component in the sample; wherein the analysis receptacle (7) is connected with the outside atmosphere in such a manner that a pressure compensation can take place.

2. Method as claimed in claim 1 wherein the connection with the outside atmosphere is only established after the adapter (10) has been attached to the analysis receptacle (7).

3. Method as claimed in claim 1 wherein for the pressure compensation the analysis receptacle (7) is perforated with a ventilation tube.

4. Method as claimed in claim 1 wherein the sample receptacle (2) is heated after the sample (5) has been filled in, in particular it is heated in such a way that a component that is not to be analyzed is expelled.

5. Method as claimed in claim 4 wherein before being heated the sample receptacle (2) is supplied with an expulsion reagent which supports the expulsion of the component that is not to be analyzed.

6. Test kit for the qualitative analysis of a gaseous component or of a component that can be transformed into gaseous form (23) of a sample (5),
   comprising:
   a sample receptacle (2) having a receptacle opening for receiving a sample (5)
   an analysis receptacle (7) having a receptacle opening for receiving a component of the sample that is to be analyzed (23) and a tracer reagent (8), and said analysis receptacle having a pressure relief device (13) for selectively connecting said analysis receptacle with the outside atmosphere, said analysis receptacle usable as a measuring receiving flask in an optical measuring instrument (25); and
   an adapter (10) which is used to connect the receptacle openings with each other so that said analysis receptacle (8) is selectively connectable with the outside atmosphere via pressure relief device (13), allowing a pressure compensation while the component is expelled from said sample receptacle into said analysis receptacle.

7. Test kit as claimed in claim 6 wherein the pressure relief device (13) is arranged on the end of the analysis receptacle (7) that is opposite to the receptacle opening (4).

8. Test kit as claimed in claim 7 wherein the pressure relief device (13) is only permeable for gases.

9. Test kit as claimed in claim 6 wherein the pressure relief device (13) is realized as a receptacle opening (15) that is closed off with a semi-permeable covering (17).

10. Test kit as claimed in claim 9 wherein the covering (17) consists of a hydrophobic material.

11. Test kit as claimed in claim 9 wherein the covering (17) is realized as a membrane consisting of e.g. PTFE, PVDR or FEP.

12. Test kit as claimed in claim 6 wherein the pressure relief device (13) is realized as a receptacle opening (14) that is closed off with a covering (16) that can be perforated.

13. Test kit as claimed in claim 12 wherein the covering is realized as a membrane (16).

14. Test kit as claimed in claim 13 wherein the membrane consists of rubber, in particular of isobutylene-isoprene copolymer, preferably coated with PTFE or FEP.

15. Test kit as claimed in claim 12 wherein a ventilation tube (21) that can be pierced through the covering (16) forms part of the pressure relief device (13).

16. Test kit as claimed in claim 9 wherein on its outer side the covering (17, 18) is equipped with a removable or pull-off protective element (20).

17. Test kit as claimed in claim 16 wherein the covering element is realized as a paste-on protective foil (20).

18. Test kit as claimed in claim 6 wherein the adapter (10) is equipped with a separating membrane (12) that is permeable for gases.

19. Test kit as claimed in claim 18 wherein the separating membrane (12) consists of a hydrophobic material.

20. Method for the qualitative analysis of a gaseous component or of a component that can be transformed into gaseous form (23) of a sample (5), comprising the steps of:
   supplying a sample to a sample receptacle (2);
   supplying a tracer reagent to an analysis receptacle (7), the analysis receptacle (7) being selectively connectable with the outside atmosphere via a pressure relief device;

connecting the receptacles via an adapter (10);

expelling a gaseous component (23) of the sample from the sample receptacle (2) into the analysis receptacle (7), while selectively connecting the analysis receptacle (7) with the outside atmosphere via the pressure relief device so that pressure compensation takes place; and analyzing color change of the tracer reagent in the analysis receptacle.

21. Test kit for the analysis of a gaseous component or of a component that can be transformed into gaseous form (23) of a sample (5) consisting of a sample receptacle (2) for receiving the sample (5) through a receptacle opening (4) and of an analysis receptacle (7) for receiving the component that is to be analyzed (23) through a receptacle opening (4), and the analysis receptacle (7) contains a tracer reagent (8) or can be supplied with a tracer reagent (8) and can be used as a measuring receiving flask in an optical measuring instrument (25), and of an adapter (10) which is used to connect the receptacle openings (4) with each other wherein the analysis receptacle (8) is equipped with a pressure relief device (13), wherein the pressure relief device (13) is arranged on an end of the analysis receptacle (7) that is opposite to the receptacle opening (4).

22. Test kit for the analysis of a gaseous component or of a component that can be transformed into gaseous form (23) of a sample (5) consisting of a sample receptacle (2) for receiving the sample (5) through a receptacle opening (4) and of an analysis receptacle (7) for receiving the component that is to be analyzed (23) through a receptacle opening (4), and the analysis receptacle (7) contains a tracer reagent (8) or can be supplied with a tracer reagent (8) and can be used as a measuring receiving flask in an optical measuring instrument (25), and of an adapter (10) which is used to connect the receptacle openings (4) with each other wherein the analysis receptacle (8) is equipped with a pressure relief device (13), wherein the pressure relief device (13) is realized as a receptacle opening (15) that is closed off with a semi-permeable covering (17).

23. Test kit for the analysis of a gaseous component or of a component that can be transformed into gaseous form (23) of a sample (5) consisting of a sample receptacle (2) for receiving the sample (5) through a receptacle opening (4) and of an analysis receptacle (7) for receiving the component that is to be analyzed (23) through a receptacle opening (4), and the analysis receptacle (7) contains a tracer reagent (8) or can be supplied with a tracer reagent (8) and can be used as a measuring receiving flask in an optical measuring instrument (25), and of an adapter (10) which is used to connect the receptacle openings (4) with each other wherein the analysis receptacle (8) is equipped with a pressure relief device (13), wherein the pressure relief device (13) is realized as a receptacle opening (14) that is closed off with a covering (16) that can be perforated.

24. The method of claim 1, wherein the analysis receptacle (7) is connected with the outside atmosphere in such a manner that a pressure compensation can take place while the component is being expelled into the analysis receptacle.

* * * * *